(12) United States Patent
Thramann et al.

(10) Patent No.: US 7,959,653 B2
(45) Date of Patent: Jun. 14, 2011

(54) SPINAL ROD CROSS CONNECTOR

(75) Inventors: Jeffery Thramann, Longmont, CO (US); Michael Fulton, Superior, CO (US)

(73) Assignee: Lanx, Inc., Broomfield, CO (US)

( * ) Notice: Subject to any disclaimer, the term of this patent is extended or adjusted under 35 U.S.C. 154(b) by 489 days.

(21) Appl. No.: 11/217,787

(22) Filed: Aug. 31, 2005

(65) Prior Publication Data

US 2006/0064093 A1 Mar. 23, 2006

Related U.S. Application Data

(60) Provisional application No. 60/607,231, filed on Sep. 3, 2004.

(51) Int. Cl.
*A61B 17/70* (2006.01)
(52) U.S. Cl. ...................................... 606/250
(58) Field of Classification Search .................. 606/61
See application file for complete search history.

(56) References Cited

U.S. PATENT DOCUMENTS

| 5,000,165 A | 3/1991 | Watanabe |
| 5,084,049 A | 1/1992 | Asher et al. |
| 5,133,717 A | 7/1992 | Chopin |
| 5,147,360 A | 9/1992 | Dubousset |
| 5,275,600 A | 1/1994 | Allard et al. |
| 5,312,405 A | 5/1994 | Korotko et al. |
| 5,334,203 A * | 8/1994 | Wagner ............... 606/252 |
| 5,374,267 A | 12/1994 | Siegal |
| 5,380,325 A | 1/1995 | Lahille et al. |
| 5,382,248 A | 1/1995 | Jacobson et al. |
| 5,387,212 A | 2/1995 | Yuan et al. |
| 5,429,639 A | 7/1995 | Judet |
| 5,437,669 A | 8/1995 | Yuan et al. |
| 5,437,671 A | 8/1995 | Lozier et al. |
| 5,468,241 A | 11/1995 | Metz-Stavenhagen et al. |
| 5,487,742 A | 1/1996 | Cotrel |
| 5,507,745 A | 4/1996 | Logroscino et al. |
| 5,514,132 A | 5/1996 | Csernatony et al. |
| 5,522,816 A | 6/1996 | Dinello et al. |
| 5,527,314 A | 6/1996 | Brumfield et al. |

(Continued)

OTHER PUBLICATIONS

International Searching Authority, "Notification of Transmittal of the International Search Report and the Written Opinion of the International Searching Authority, or the Declaration", Mar. 14, 2008.

*Primary Examiner* — Eduardo C Robert
*Assistant Examiner* — Mary Hoffman
(74) *Attorney, Agent, or Firm* — Holland & Hart LLP

(57) ABSTRACT

The cross connecting device includes a bar arm coupled to one of a pair of posterior rods or spinal fixation rods and a rod arm coupled to the other of the pair of the rods. The bar arm and rod arm are coupled together by a connector or coupling device. The coupling device has a shank extending through a bore in the bar arm and a connector bore through which a protrusion on the bar arm extends. The bar arm is rotationally movable in the connector bore. The shank is rotationally and translationally movable in the bar arm bore. The coupling device is vertically movable through the bore. The protrusion is rotationally and translationally movable in the connector bore. The cross connecting devices are coupled to the rods by a pair of opposing surface to surface contacts formed by a surface of a hook end and a surface of a pad.

11 Claims, 9 Drawing Sheets

U.S. PATENT DOCUMENTS

| | | | |
|---|---|---|---|
| 5,534,002 A | 7/1996 | Brumfield et al. | |
| 5,542,946 A | 8/1996 | Logroscino et al. | |
| 5,562,662 A | 10/1996 | Brumfield et al. | |
| 5,569,246 A | 10/1996 | Ojima et al. | |
| 5,601,552 A | 2/1997 | Cotrel | |
| 5,607,425 A * | 3/1997 | Rogozinski | 606/61 |
| 5,609,592 A | 3/1997 | Brumfield et al. | |
| 5,624,442 A | 4/1997 | Mellinger et al. | |
| 5,651,789 A | 7/1997 | Cotrel | |
| 5,667,506 A | 9/1997 | Sutterlin | |
| 5,669,910 A | 9/1997 | Korhonen et al. | |
| 5,688,272 A | 11/1997 | Montague et al. | |
| 5,693,053 A | 12/1997 | Estes | |
| 5,702,395 A | 12/1997 | Hopf | |
| 5,702,452 A | 12/1997 | Argenson et al. | |
| 5,716,355 A | 2/1998 | Jackson et al. | |
| 5,743,911 A | 4/1998 | Cotrel | |
| 5,752,955 A | 5/1998 | Errico | |
| 5,782,833 A | 7/1998 | Haider | |
| 5,800,548 A | 9/1998 | Martin et al. | |
| 5,814,046 A | 9/1998 | Hopf | |
| 5,899,903 A | 5/1999 | Cotrel | |
| 5,947,966 A | 9/1999 | Drewry et al. | |
| 5,954,725 A | 9/1999 | Sherman et al. | |
| 5,980,521 A | 11/1999 | Montague et al. | |
| 5,980,523 A * | 11/1999 | Jackson | 606/61 |
| 5,984,922 A | 11/1999 | McKay | |
| 5,989,250 A | 11/1999 | Wagner et al. | |
| 5,989,251 A | 11/1999 | Nichols | |
| 6,004,322 A | 12/1999 | Bernstein | |
| 6,015,409 A | 1/2000 | Jackson | |
| 6,083,226 A | 7/2000 | Fiz | |
| 6,096,039 A | 8/2000 | Stoltenberg et al. | |
| 6,110,173 A | 8/2000 | Thomas, Jr. | |
| 6,113,600 A | 9/2000 | Drummond et al. | |
| 6,132,430 A | 10/2000 | Wagner | |
| 6,136,003 A | 10/2000 | Hoeck et al. | |
| 6,139,548 A | 10/2000 | Errico | |
| 6,171,311 B1 | 1/2001 | Richelsoph | |
| 6,179,838 B1 | 1/2001 | Fiz | |
| 6,217,578 B1 * | 4/2001 | Crozet et al. | 606/61 |
| 6,234,705 B1 | 5/2001 | Troxell | |
| 6,238,396 B1 | 5/2001 | Lombardo | |
| 6,283,967 B1 | 9/2001 | Troxell et al. | |
| 6,299,614 B1 | 10/2001 | Kretschmer et al. | |
| 6,302,882 B1 | 10/2001 | Lin et al. | |
| 6,306,137 B2 | 10/2001 | Troxell | |
| 6,328,740 B1 | 12/2001 | Richelsoph | |
| 6,328,741 B1 | 12/2001 | Richelsoph | |
| 6,368,320 B1 | 4/2002 | Le Couedic et al. | |
| 6,379,354 B1 | 4/2002 | Rogozinski | |
| 6,402,751 B1 | 6/2002 | Hoeck et al. | |
| 6,413,258 B1 | 7/2002 | Bernhardt, Jr. | |
| 6,416,515 B1 | 7/2002 | Wagner | |
| 6,432,108 B1 | 8/2002 | Burgess et al. | |
| 6,468,276 B1 | 10/2002 | McKay | |
| 6,520,444 B1 | 2/2003 | Muller | |
| 6,524,310 B1 | 2/2003 | Lombardo et al. | |
| 6,547,789 B1 * | 4/2003 | Ventre et al. | 606/61 |
| 6,554,832 B2 | 4/2003 | Shluzas | |
| 6,562,040 B1 | 5/2003 | Wagner | |
| 6,589,243 B1 | 7/2003 | Viart et al. | |
| 6,595,992 B1 | 7/2003 | Wagner et al. | |
| 6,602,253 B2 | 8/2003 | Richelsoph et al. | |
| 6,616,668 B2 | 9/2003 | Altarac et al. | |
| 6,626,909 B2 | 9/2003 | Chin | |
| 6,645,207 B2 | 11/2003 | Dixon et al. | |
| 6,673,073 B1 * | 1/2004 | Schafer | 606/61 |
| 6,716,213 B2 | 4/2004 | Shitoto | |
| 6,736,817 B2 | 5/2004 | Troxell et al. | |
| 6,752,807 B2 | 6/2004 | Lin et al. | |
| 6,761,721 B2 | 7/2004 | Burgess et al. | |
| 6,783,526 B1 | 8/2004 | Lin et al. | |
| 6,786,907 B2 | 9/2004 | Lange | |
| 6,802,844 B2 | 10/2004 | Ferree | |
| 6,872,208 B1 | 3/2005 | McBride et al. | |
| 6,875,211 B2 | 4/2005 | Nichols et al. | |
| 6,887,241 B1 | 5/2005 | McBride et al. | |
| 7,122,036 B2 | 10/2006 | Vanacker | |
| 7,137,986 B2 | 11/2006 | Troxell et al. | |
| 7,160,301 B2 | 1/2007 | Cordaro | |
| 7,166,108 B2 | 1/2007 | Mazda et al. | |
| 7,166,109 B2 | 1/2007 | Biedermann et al. | |
| 2001/0047171 A1 | 11/2001 | Troxell et al. | |
| 2002/0007183 A1 | 1/2002 | Lee et al. | |
| 2002/0032442 A1 | 3/2002 | Altarac et al. | |
| 2002/0040223 A1 | 4/2002 | Sato et al. | |
| 2002/0052603 A1 | 5/2002 | Nichols et al. | |
| 2002/0111625 A1 * | 8/2002 | Richelsoph et al. | 606/61 |
| 2002/0138077 A1 | 9/2002 | Ferree | |
| 2002/0143327 A1 | 10/2002 | Shluzas | |
| 2002/0143330 A1 | 10/2002 | Shluzas | |
| 2002/0169448 A1 | 11/2002 | Vanacker | |
| 2002/0169450 A1 | 11/2002 | Lange | |
| 2002/0183749 A1 | 12/2002 | Burgess et al. | |
| 2003/0018334 A1 | 1/2003 | Richelsoph et al. | |
| 2003/0045874 A1 | 3/2003 | Thomas, Jr. | |
| 2003/0078580 A1 | 4/2003 | Shitoto | |
| 2003/0083659 A1 | 5/2003 | Lin et al. | |
| 2003/0114853 A1 | 6/2003 | Burgess et al. | |
| 2003/0125742 A1 | 7/2003 | Yuan et al. | |
| 2003/0163132 A1 | 8/2003 | Chin | |
| 2003/0171751 A1 | 9/2003 | Ritland | |
| 2004/0015166 A1 | 1/2004 | Gorek | |
| 2004/0049188 A1 | 3/2004 | Slivka et al. | |
| 2004/0116928 A1 * | 6/2004 | Young et al. | 606/61 |
| 2004/0122425 A1 | 6/2004 | Suzuki et al. | |
| 2004/0133202 A1 | 7/2004 | Suzuki et al. | |
| 2004/0133203 A1 * | 7/2004 | Young et al. | 606/61 |
| 2004/0172024 A1 | 9/2004 | Gorek | |
| 2004/0176766 A1 | 9/2004 | Shluzas | |
| 2004/0181223 A1 | 9/2004 | Ritland | |
| 2004/0260287 A1 | 12/2004 | Ferree | |
| 2005/0010222 A1 | 1/2005 | Cordaro | |
| 2005/0033295 A1 | 2/2005 | Wisnewski | |
| 2005/0090821 A1 * | 4/2005 | Berrevoets et al. | 606/61 |
| 2005/0107789 A1 | 5/2005 | Sweeney | |
| 2005/0113830 A1 | 5/2005 | Rezach et al. | |
| 2005/0137594 A1 | 6/2005 | Doubler et al. | |
| 2005/0149019 A1 | 7/2005 | Sasing et al. | |
| 2005/0149023 A1 | 7/2005 | Ritland | |
| 2005/0154390 A1 | 7/2005 | Biedermann et al. | |
| 2005/0228377 A1 | 10/2005 | Chao et al. | |
| 2006/0036240 A1 | 2/2006 | Colleran et al. | |
| 2006/0079892 A1 | 4/2006 | Roychowdhury et al. | |
| 2006/0206114 A1 | 9/2006 | Ensign et al. | |
| 2006/0229607 A1 | 10/2006 | Brumfield | |
| 2006/0241598 A1 | 10/2006 | Khalili | |
| 2006/0241602 A1 | 10/2006 | Jackson | |
| 2006/0247626 A1 | 11/2006 | Taylor et al. | |
| 2006/0271045 A1 | 11/2006 | Hubbard et al. | |
| 2006/0271051 A1 | 11/2006 | Berrevoets et al. | |
| 2007/0016197 A1 | 1/2007 | Woods et al. | |
| 2007/0049932 A1 | 3/2007 | Richelsoph et al. | |

* cited by examiner

SPINAL ROD CROSS CONNECTOR

RELATED APPLICATION

This application claims priority to U.S. Provisional Patent Application Ser. No. 60/607,231, titled SPINAL ROD CROSS CONNECTOR, filed Sep. 3, 2004, incorporated herein by reference as if set out in full. This application is related to co-pending U.S. patent application Ser. No. 10/915,902, titled SCREW AND ROD FIXATION SYSTEM, filed Aug. 10, 2004, and incorporated herein by reference as if set out in full.

FIELD OF THE INVENTION

The present invention relates to devices useful in correcting spinal abnormalities and, more particularly, the invention is related to a cross connector that enhances the rigidity and stability of the devices useful in correcting spinal abnormalities.

BACKGROUND OF THE INVENTION

As is generally known in the art, spinal abnormalities may be correctable using a pair of posterior spinal fixation rods attached to the vertebrae using pedicle screws and the like. One such spinal fixation system is described in co-pending, related application Ser. No. 10/915,902 mentioned above.

In order to provide increased stability and rigidity, especially to resist twisting or the like, the pair of elongated rods often includes cross-connecting devices. The cross connecting devices typically traverse the spinal column and couple to each of the elongated rods. In other words, the cross connecting devices are perpendicular or substantially perpendicular to the spinal column.

One difficulty with connecting the elongated rods using cross-connecting devices resides in the fact that the pair of elongated rods is not exactly parallel and equally spaced along the spine. The cross connecting devices typically comprises at least two separate portions that couple together to compensate for these deviations. To couple the separate parts of the cross connecting device together, a coupling device must be provided that has a plurality of degrees of freedom so the cross connecting devices can be rotationally, angularly, and vertically oriented to compensate for the deviations.

While providing separate devices provides a satisfactory solution relating to the coupling the cross connecting devices to the pair of elongated rods, it causes different problems. One such problem, for example, is that the force required to satisfactorily connect to separate devices provides stresses to the cross connecting devices that may cause twisting and bending of the pair of elongated rods. Thus, it would be desirous to develop an improved cross connector that addresses this and other problems associated with the prior art.

SUMMARY OF THE INVENTION

To attain the advantages and in accordance with the purpose of the invention, as embodied and broadly described herein a cross connecting device is provided. The cross connecting device includes a bar arm coupled to one of a pair of posterior rods or spinal fixation rods and a rod arm coupled to the other of the pair of the rods. The bar arm and rod arm are coupled together by a connector or coupling device. The coupling device has a shank extending through a bore in the bar arm and a connector bore through which a protrusion on the bar arm extends. The bar arm is rotationally movable in the connector bore. The shank is rotationally and translationally movable in the bar arm bore. The coupling device is vertically movable through the bore. The protrusion is rotationally and translationally movable in the connector bore.

The foregoing and other features, utilities and advantages of the invention will be apparent from the following more particular description of a preferred embodiment of the invention as illustrated in the accompanying drawings.

BRIEF DESCRIPTION OF THE DRAWING

The accompanying drawings illustrate various embodiments of the present invention and are a part of the specification. The illustrated embodiments are merely examples and illustrations of the present invention and do not limit the scope of the invention.

DETAILED DESCRIPTION

The present invention relates to a device that traverses a spinal column to connect a pair of elongated rods being used to correct spinal abnormalities, such as, for example, spinal curvature.

Figure 1:
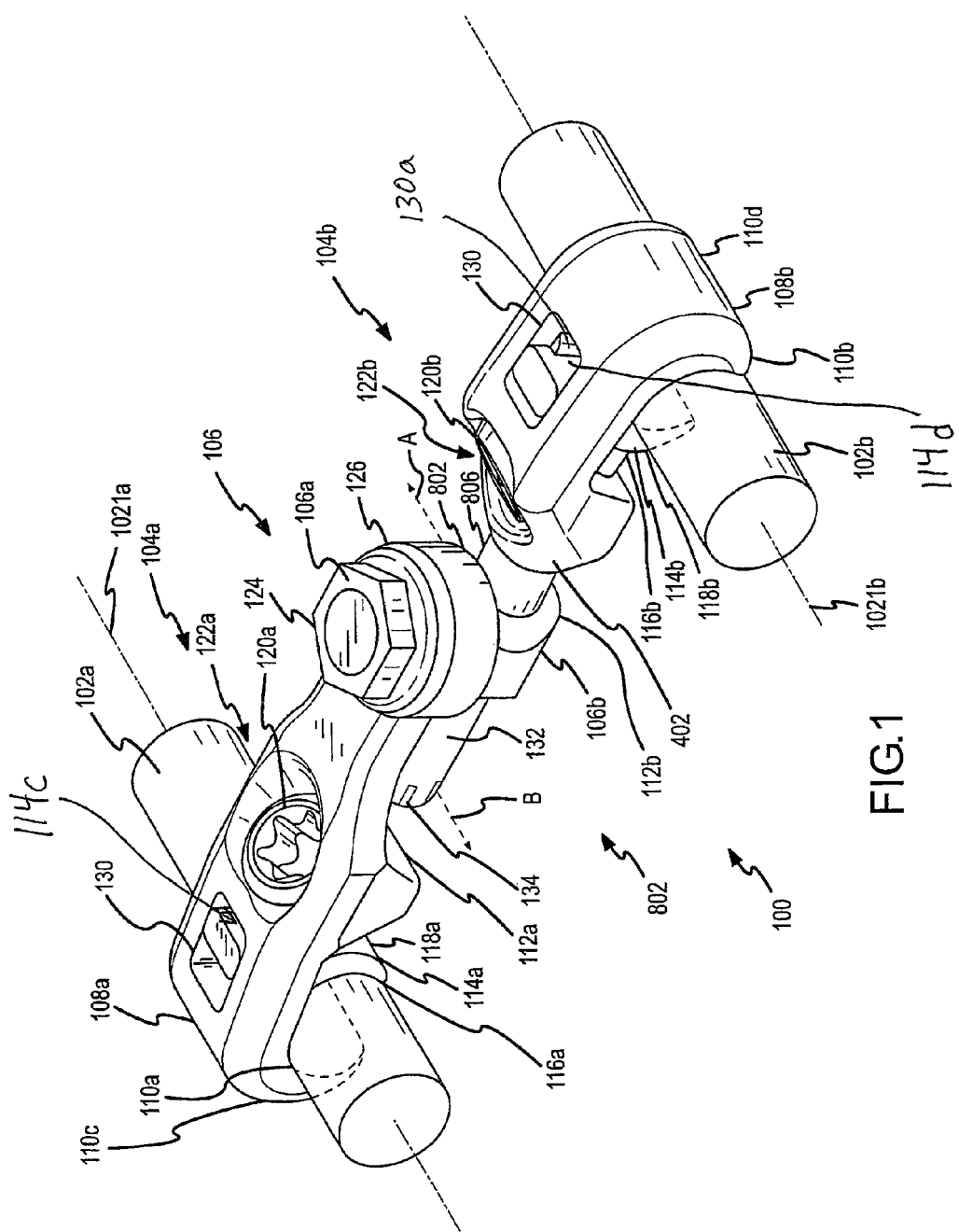
FIG. 1 is a top perspective view of a cross connect device consistent with an embodiment of the present invention.

Referring now to FIG. 1, a top perspective view of a cross connector 100 is shown. Cross connector 100 is shown attached to a pair of elongated spinal fixation rods 102a and 102b. Spinal fixation rods 102a and 102b would be connected to the pedicle portion of vertebral bodies about the spinal column as is generally known in the art (not shown). Related application Ser. No. 10/915,902 mentioned above describes a novel device for attaching spinal fixation rods 102a and 102b to the pedicles.

Cross connector 100 comprises at least two independently movable parts coupled together. A first part 104a, sometimes referred to as bar arm 104a, connected to spinal fixation rod 102a and a second part 104b, sometimes referred to as rod arm 104b, connected to spinal fixation rod 104b. Bar arm 104a is shown in more detail in FIGS. 2A, 2B, and 3. Rod arm 104b is shown in more detail in FIG. 4. Bar arm 104a is coupled to second part 104b using a coupling device 106. Coupling device 106 comprises a nut 106a and a bolt 106b. Coupling device 106 is shown in more detail in FIGS. 5-7.

Bar arm 104a has a hook 108a that has an inner surface 110a shaped to cooperatively engage spinal fixation rod 102a. While referred to as hook 108a because the particular embodiment is shaped as similar to a fish hook, one of ordinary skill in the art would recognize that hook is used generically to refer to numerous shapes. In this case, inner surface 110a has a concave shape to provide a surface-to-surface engagement with a convexly shaped rod 102a. An outer surface 110c of hook 108a does not need to be convexly shaped as shown, but it is believed the smooth curve would reduce trauma. Extending from hook 108a is a first arm 112a traversing a portion of the spinal column (not shown). First arm 112a is shown with a generally cubic shape, but other shapes are possible. Coupled to first part 104a is a first rod grip insert or cross connector pad 114a (sometimes referred to as simply pad 114a). Pad 114a is somewhat moveable between a grip position (as shown) and a release position. Pad 114a has a rod contact surface 116a shaped to cooperatively engage spinal fixation rod 102a and a setscrew contact surface 118a shaped to cooperatively engage a first setscrew 120a. First setscrew 120a is threadable into a first bore 122a traversing first arm 112a at an acute angle α (shown in FIG. 2). First setscrew 120a can be tightened to impinge on setscrew contact surface 118a to cause pad 114a to engage rod 102a such that rod contact surface 116a provides a surface-to-surface contact between rod contact surface 116a, and spinal fixation rod 102a. Moreover, first setscrew 120a impinging on setscrew contact surface 118a tends to cause first rod grip insert 114a to transmit compressive force to spinal fixation rod 102a to seat spinal fixation rod 102a on first inner surface 110a, which provides another surface-to-surface contact that is between rod 102a and first inner surface 110a.

Bar arm 104a provides a stable connection for cross connector 100 to rod 102a through the at least the two surface-to-surface contacts identified. Reverse threading setscrew 120a allows pad 114a to be moved to the release position such that cross connecting device 100 can be fitted or removed from spinal fixation rod 102a. In other words, reverse threading setscrew 120a releases the compressive force tending to seat the construct. To facilitate movement between grip and release positions, pad 114a may be coupled to first part 104a using a channel, slot, or groove 130 that provides a plurality of positions for first rod grip insert 114a.

Referring now to FIGS. 1, 2A, 2B and 4, there is shown pad 114a disposed in slot 130 to provide for the plurality of positions for first rod grip insert 114a. As can be seen in bar arm 104b (FIGS. 1 and 4) and bar arm 104a (FIGS. 2A and 2B), in the illustrated embodiment groove 130 may be provided with a ledge 130a or other engagement surface for movement of pad 114a between a grip position and a release position with respect to a spinal fixation rod.

Referring to FIG. 1, pads 114a, 114b may each include a necked-down portions 114c, 114d, respectively. Necked-down portion 114d may cooperatively engage with ledge 130a so as to allow translation of pad 114b.

The surface-to-surface contacts between inner surface 110a and rod contact surface 116a provide a clamp type of coupling between first part 104a and spinal fixation rod 102a. The clamp type coupling allows first part 104a to be rotated about a longitudinal axis 1021a of spinal fixation rod 102a. This allows multiple angular orientations of the first part or bar arm 104a relative to the second part or rod arm 104b.

Figure 3:
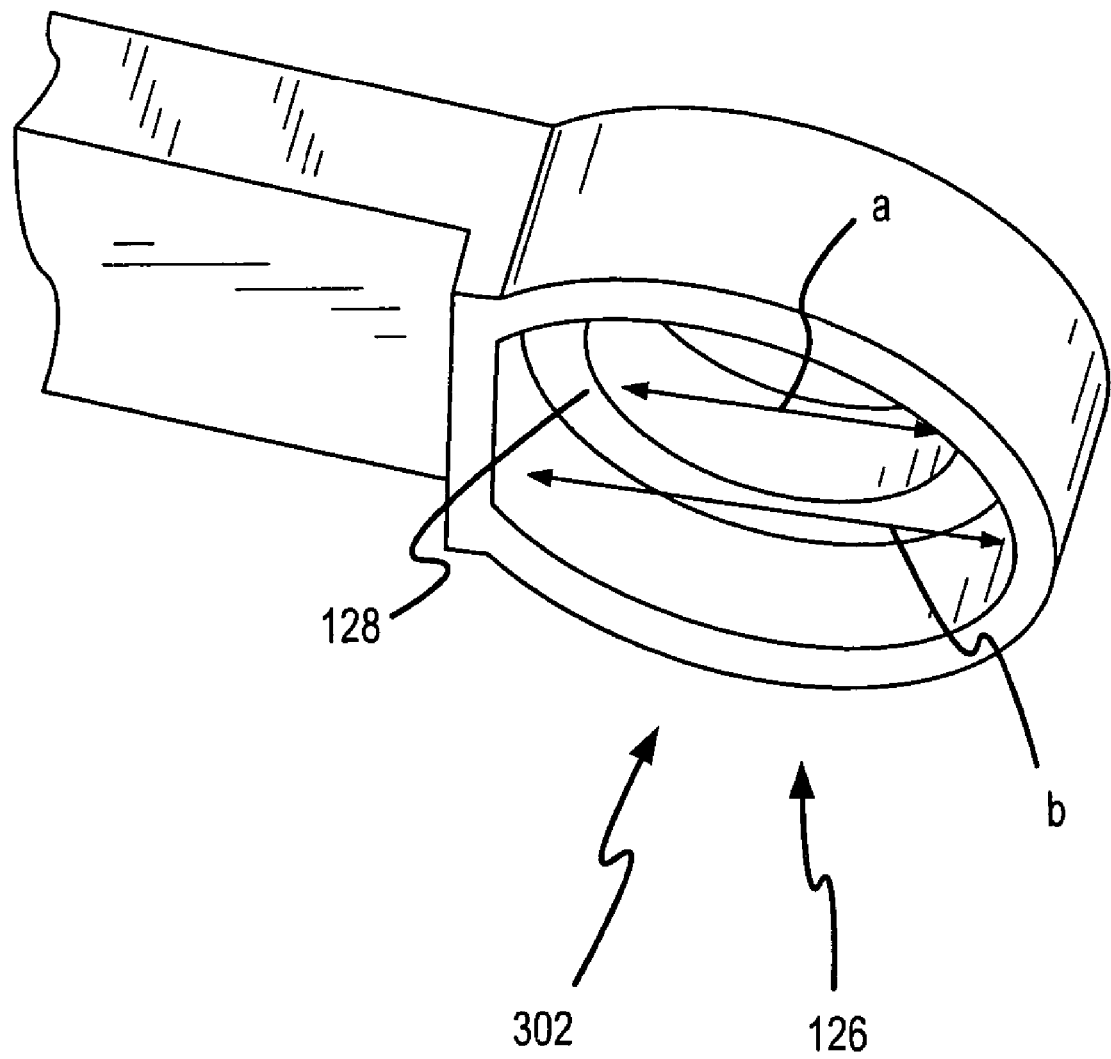
FIG. 3a is a top perspective view of connecting end 124 of first part 104a shown in FIG. 2.

As mentioned first arm 112a extends from hook 108a to partially traverse the spinal column in a first plane A. First arm 112a terminates at a connecting end 124. Connecting end 124 comprises a bore 126 extending through first arm 112a. Referring to FIG. 3, it can be seen that bore 126 comprises a first diameter a and a second diameter b. The different diameters provide a shoulder 128. Bore 126 and shoulder 128 define a recess 302 or chamber as will be explained further below. Coupling device 106 interacts with recess 302, or with bore 126 and shoulder 128, as will be explained below.

Figure 4:
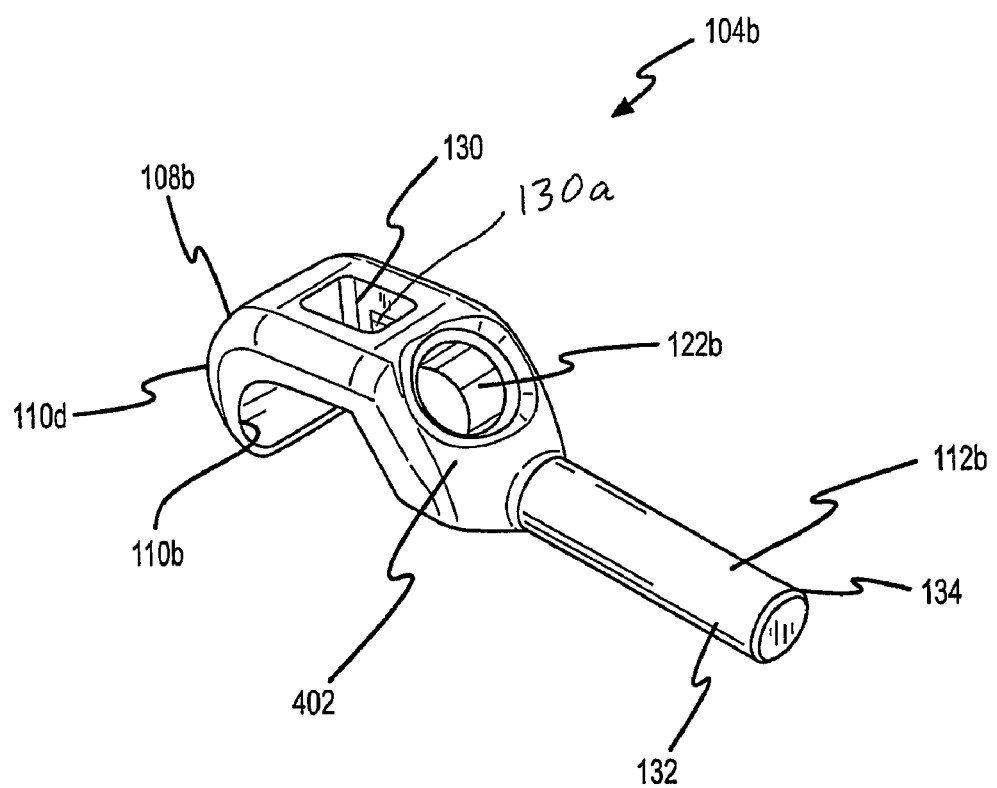
FIG. 4 is a top perspective view of a second part 104b of the cross connect device of FIG. 1.

Referring now to FIGS. 1 and 4, second part or rod arm 104b will now be explained in more detail. Rod arm 104b has parts similar to bar arm 104a. The similar parts include a second hook 108b, a second inner surface 110b, a second rod grip insert 114b with a rod contact surface 116a and a setscrew contact surface 118b, a second setscrew 120b, a second bore 122b, and channel 130. Setscrew bore 122b forms an acute angle α with second arm 112b. While bores 122a and 122b are shown forming identical angles α, they could form different angles as desired.

Figure 8:
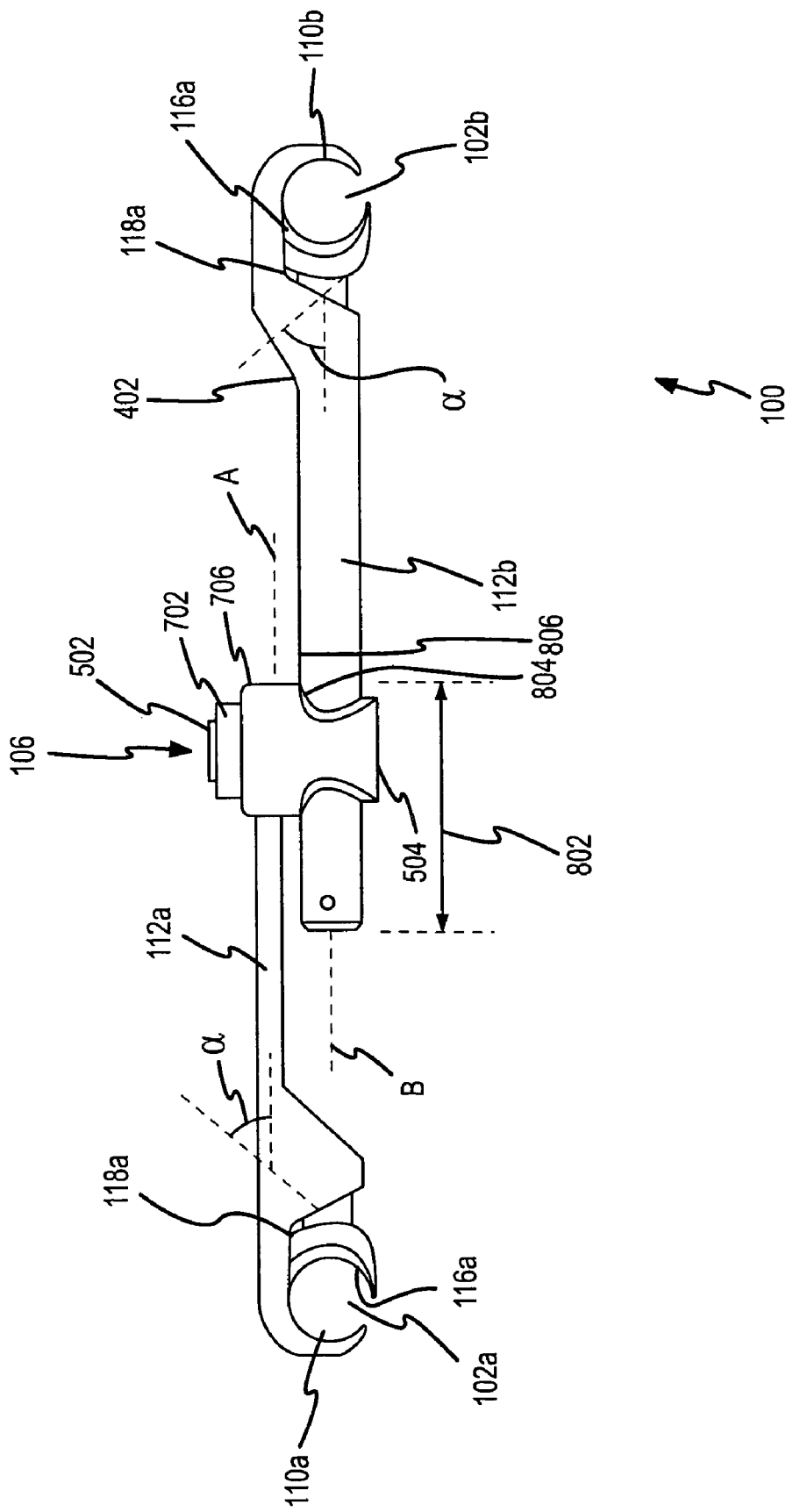
FIG. 8 is a front elevation view of the cross connect device of FIG. 1.

Unlike bar arm 104a in which first arm 112a extends substantially straight from hook 108a in plane A, rod arm 104b has a plane traversing surface 402 such that second arm 112b extends from traversing surface 402 in plane B to partially traverse the spinal column. Traversing surface 402 may extend from hook 108b to second arm 112b at an acute angle, but could be at a right angle or more. Plane traversing surface 402 could be employed to bar arm 104a and first arm 112a. Second arm 112b terminates in a male shank portion 132, which couples to coupling device 106 as will be explained further below. In this case, second arm 112b is shown substantially cylindrical, but as will be explained further below, only the male shank portion 132 needs to be cylindrical in this embodiment. Male shank portion 132 may comprises a protrusion 134 such as a detent, lip, shoulder, or ridge at a distal portion of shank portion 132. Protrusion 134 inhibits second arm 112b from decoupling from coupling device 106. As can be seen, first arm 112a and second arm 112b have an overlapping region 802 (best seen in FIG. 8). Spinal fixation rod arm 102b is contained in a clamp like coupling by hook 108b (specifically surface 110a) and pad 114b (specifically surface 116b). The clamp like coupling allows rod arm 102b to pivot about a longitudinal axis 1021b of spinal fixation rod 102b.

Figure 2A:
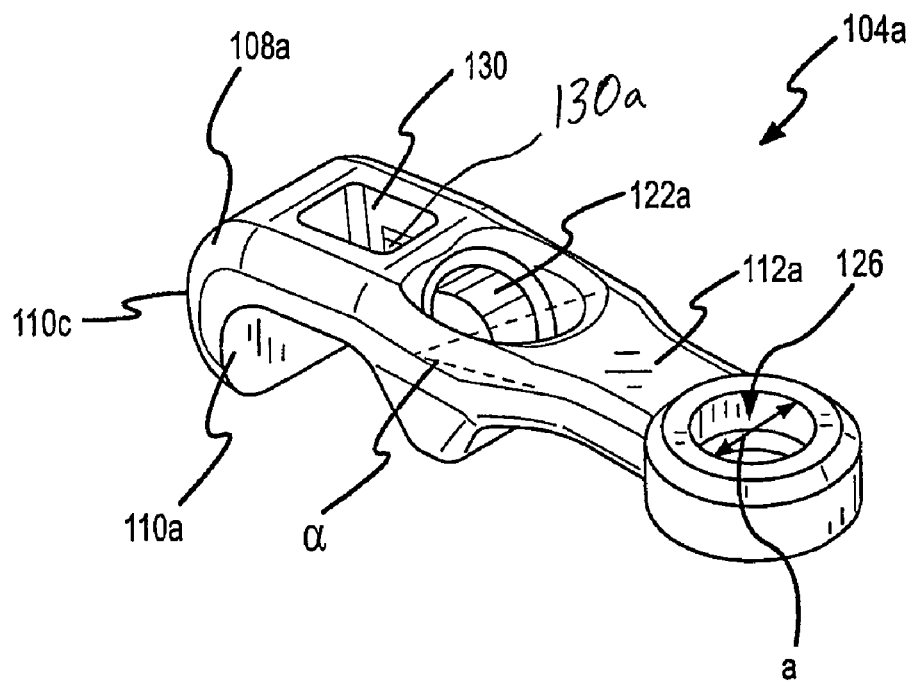
FIG. 2A is a top perspective view of the first part 104a of the cross connect device of FIG. 1.
Figure 2B:
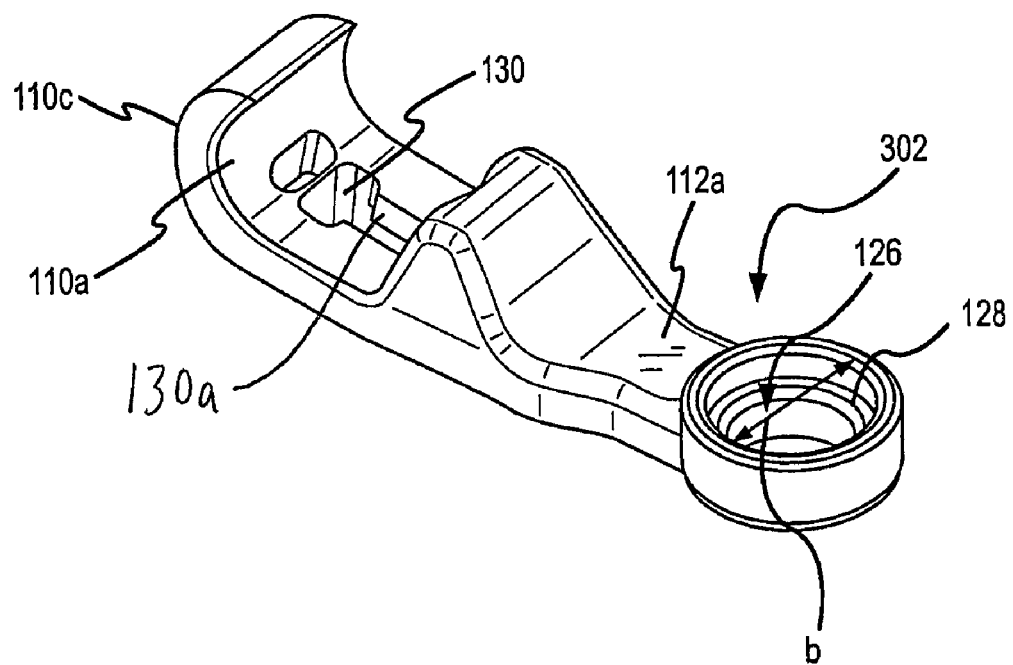
FIG. 2B is a bottom perspective view of the first part 104a of the cross connect device of FIG. 1.

FIGS. 2A and 2B show a top and bottom perspective view of bar arm 104a from FIG. 1. FIGS. 2A and 2B show parts identified above that will not be re-described herein. FIG. 3 shows a bottom perspective view of bore 126, shoulder 128, and recess 302 in more detail. FIG. 4 shows a top perspective view of rod arm 104b from FIG. 1. FIG. 4 shows parts identified above that will not be re-described herein.

Figure 5:
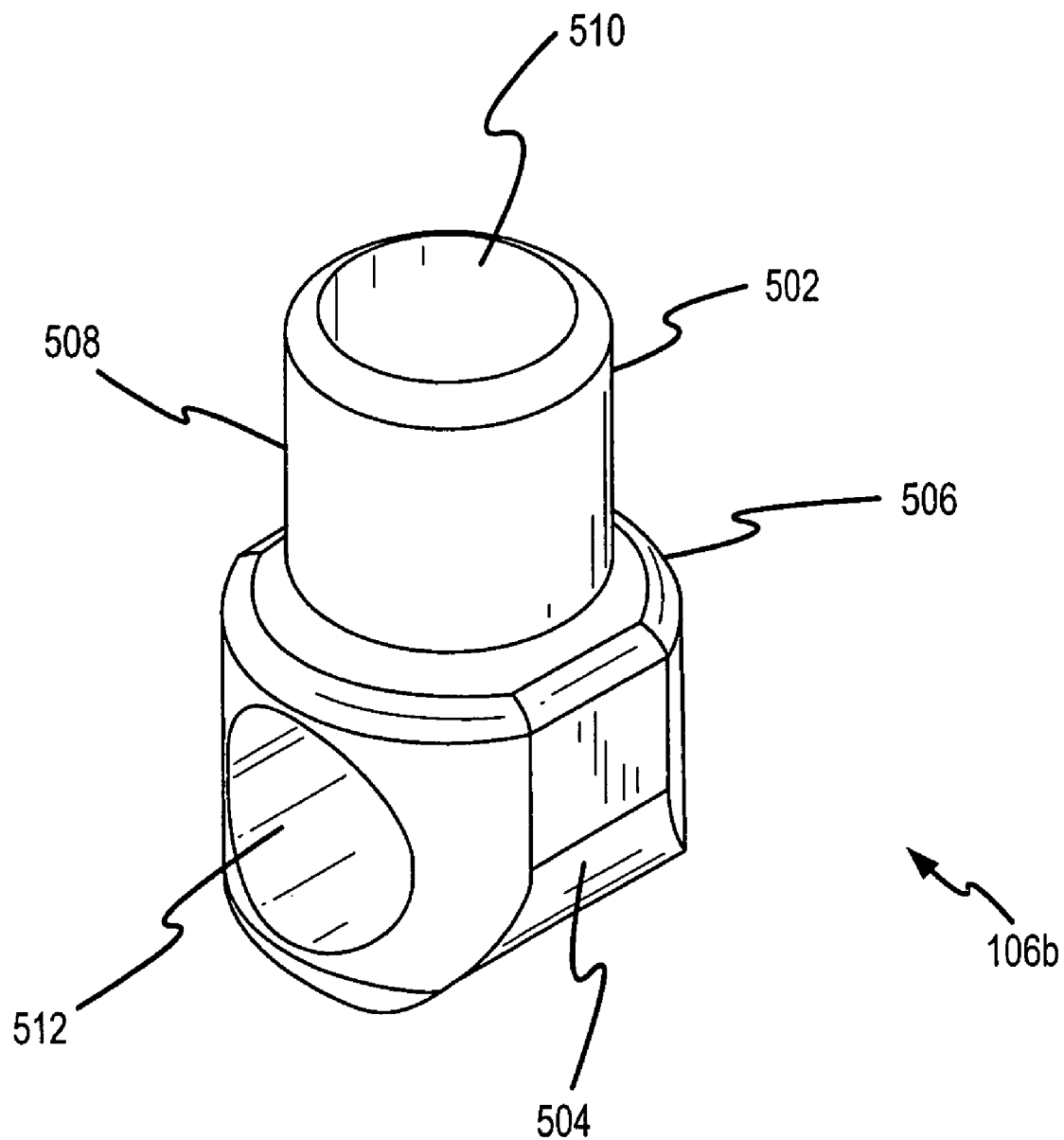
FIG. 5 is a perspective view of a bolt 106b of the cross connect device of FIG. 1.

Coupling device 106 will be described in more detail with reference to FIGS. 5-7. Referring specifically to FIG. 5, bolt 106b is shown in more detail. Bolt 106b comprises an upper shank 502, a lower socket 504, and a transition portion 506. Upper shank 502 has a threaded outer surface 508 and an inner surface 510 shaped to cooperatively engage a counter torque tool (not specifically shown). Inner surface 510 is optional and other types of counter torque devices generally known in the art or no counter torque device is possible. Lower socket 504 has a connector bore 512 that is shaped to slidably engage male shank portion 132.

Figure 6:
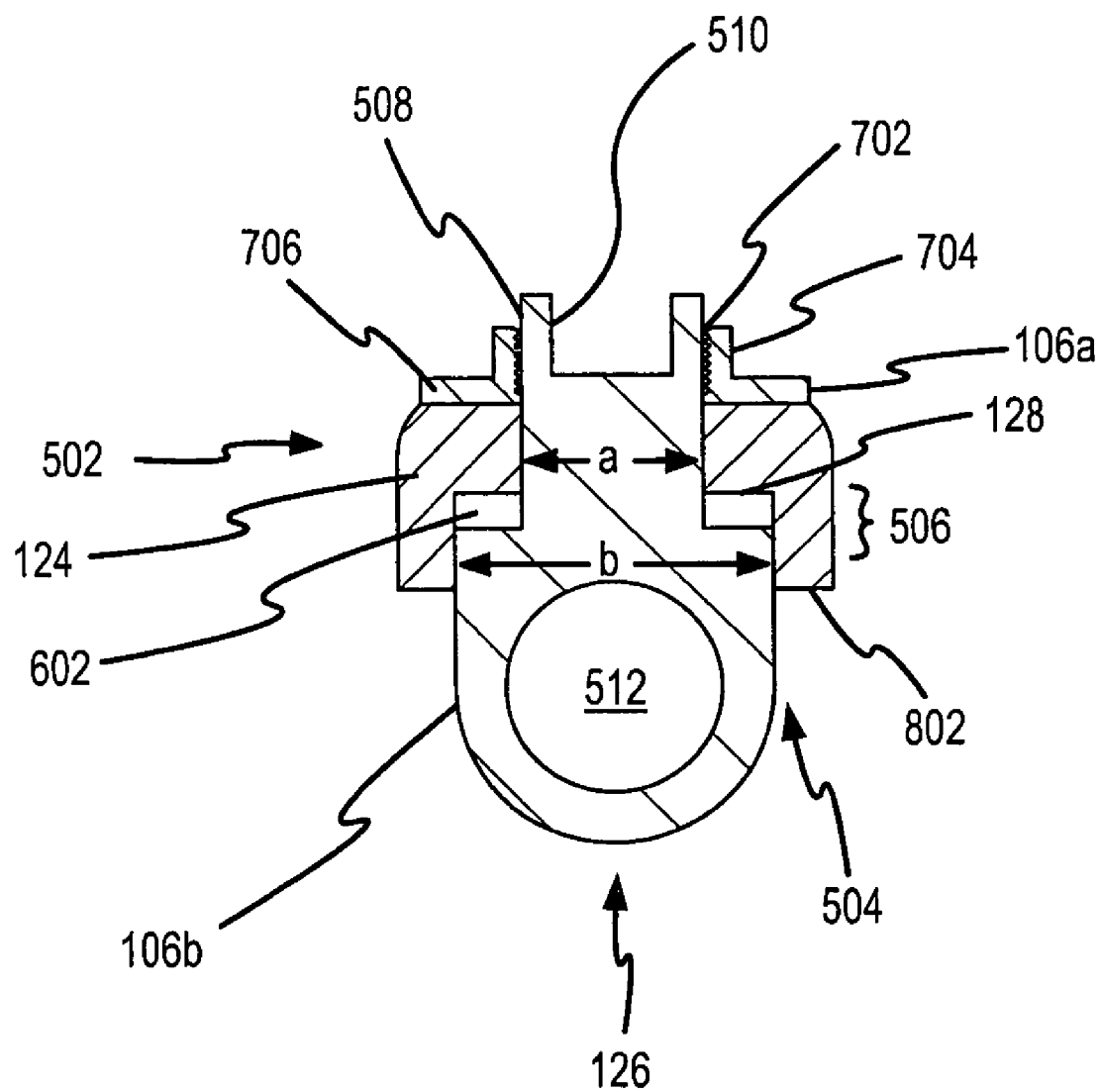
FIG. 6 is a cross sectional view of first part 104a and coupling device 106 of FIG. 1.
Figure 7:
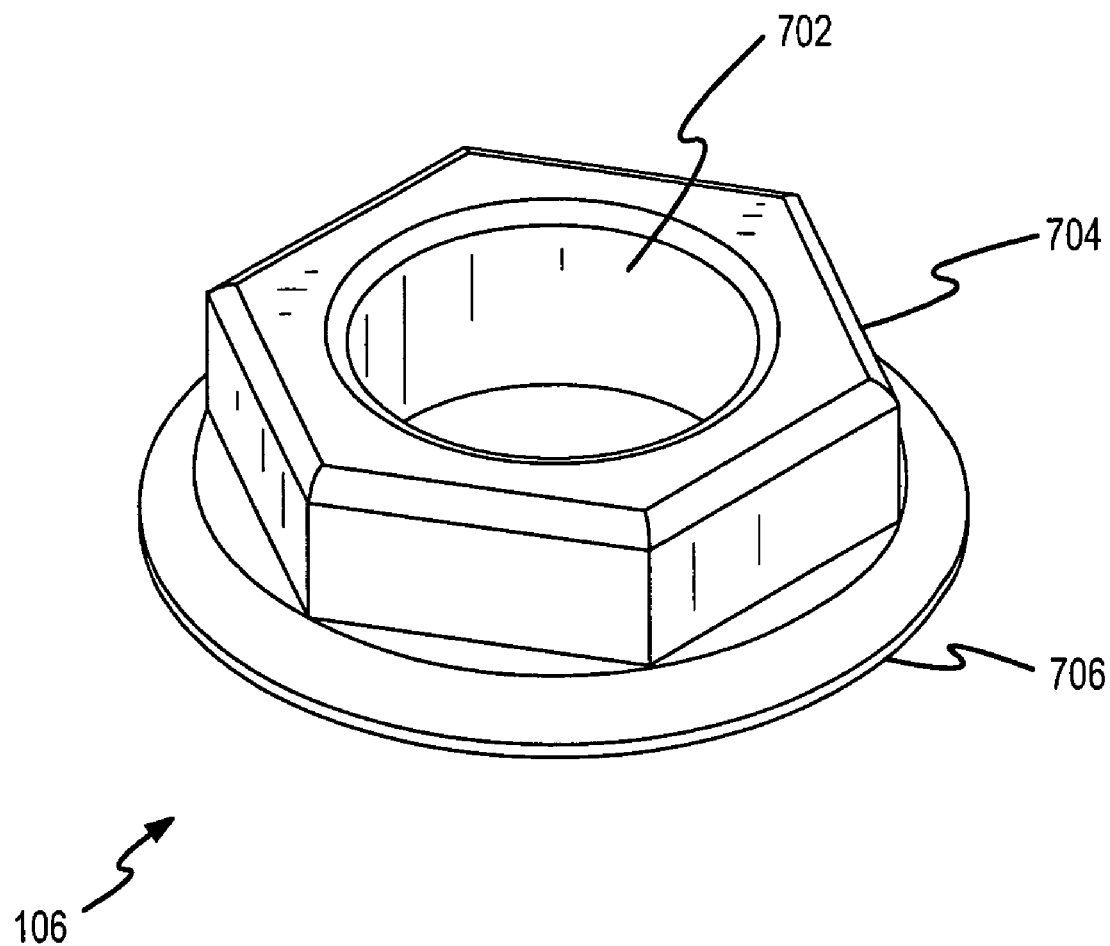
FIG. 7 is a top perspective view of a nut 106a of the cross connect device of FIG. 1.

Upper shank 502 extends through bore 126 such that at least a portion of the threaded outer surface 508 extends from arm 112a (best seen in FIG. 6). Outer surface 508 could be completely threaded or partially threaded as a matter of design choice. Upper shank 502 is sized to rotatably move in bore 126.

As mentioned above, upper shank 502 has an inner surface 510 designed to cooperatively engage a counter torque tool. In operation, nut 106a is threaded on upper shank 502 using sufficient torque to provide a sufficient seat between bar arm 104a and rod arm 104b. This torque tends to cause device 100 to want to twist or walk along spinal fixation rods 102. To inhibit this, a surgeon would use the counter torque tool to engage upper shank 502. The counter torque tool would tend to resist the torque applied to nut 106a reducing the twisting or walking.

Transition portion 506 provides a transition from the wider lower socket 504 to the narrower upper shank 502. Transition portion 506 is shown as a flat surface, but could take a number of shapes. As shown best in FIG. 6 and will be explained further below, a gap 602 resides between transition portion 506 and shoulder 128, the reasons for which will be explained below.

Nut 106a (shown in FIG. 7) has a threaded inner surface 702, an outer surface tool-engaging surface 704, and a bar arm contact surface 706. Nut 106a is threaded on upper shank 502 until bar arm contact surface 706 contacts first arm 112a.

When implanting device 100, orientation of the pair of spinal fixation rods 102 can be accommodated in various ways. For example, sliding male shank portion 132 in bore 512 can accommodate distance changes between rod 102a and 102b. Rotating male shank 132 in bore 512 compensates for angular differences between corresponding longitudinal axes 1021a and 1021b of spinal fixation rods 102a and 102b, respectively. This causes overlapping portion 802 to increase or decrease as necessary. Rotating coupling device 106 in bore 126 accommodates angular orientation differences between rods 102. Tightening nut 106a on bolt 106b causes bolt 106b to move into recess 302 until a surface 806 on rod arm 112b contact a lower edge 802 of bore 126 accommodating height differences. Angling first and second arms 112 to diverge or converge if necessary can accommodate height differences. In other words, planes A and B are not necessarily parallel planes.

Figure 9:
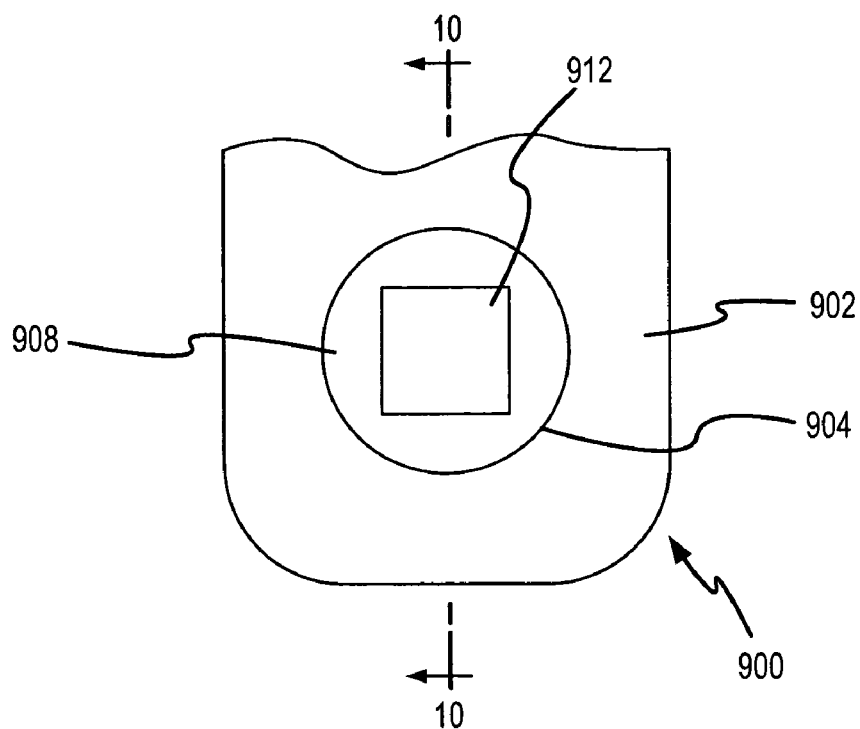
FIG. 9 is an elevation view of an alternative construction of the lower socket portion of bolt 106b.
Figure 10:
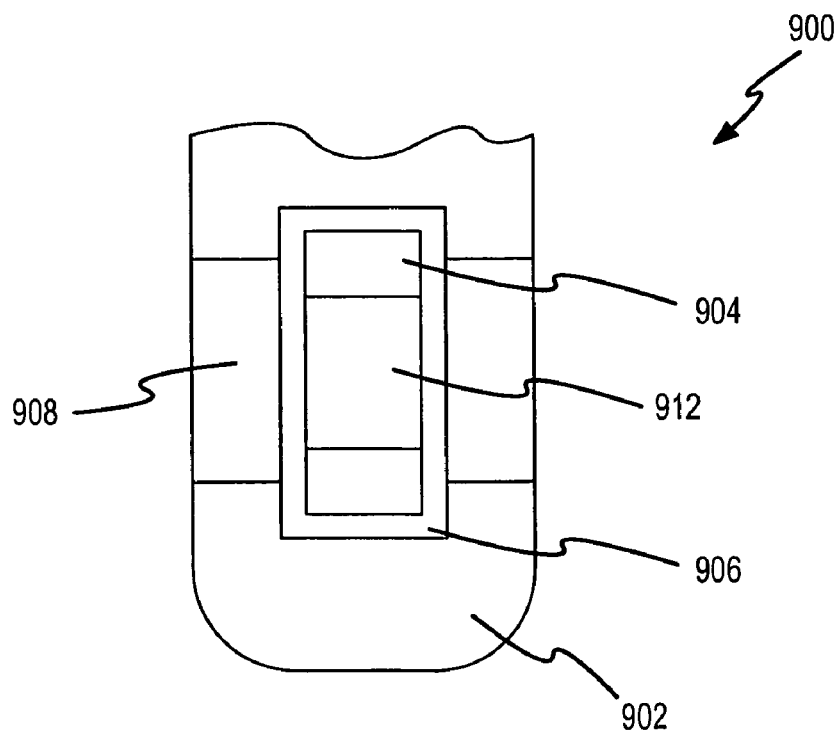
FIG. 10 is a cross sectional view of the lower socket of FIG. 9.

As explained above, male shank portion 132 is designed with a shape to cooperatively engage bore 512 to allow for rotational, slidable engagement of male shank portion 132. However, male shank portion 132 and bore 512 do not need to be cylindrical in shape. For example, referring to FIGS. 9 and 10, a square bore 908 is shown that would cooperatively engage a square male shank portion (not specifically shown, but generally similar to male shank portion 132 except for shape). In this case, bore 908 would be a part of a bolt 900 having a bore holder 902 holding a bore nut 904 (bore 912 resides in bore nut 904. A channel 906 in bore holder 902 rotationally engages bore nut 904 so the male shank portion can be rotationally oriented within bolt 900.

On reading the above disclosure, one of ordinary skill in the art would now appreciate the unique surface to surface contact between the cross connector 100 and the spinal fixation rod 102a and 102b, which connections are provided in part by surface 110a, 110c and 116a, 116b, could be used in a fixed cross-connector arrangement instead of a variable arrangement as described above. Moreover, the portion of cross connector 100 traversing the area between the rod 102a and 102b may sometimes be generically referred to as a bridge.

While the invention has been particularly shown and described with reference to an embodiments thereof, it will be understood by those skilled in the art that various other changes in the form and details may be made without departing from the spirit and scope of the invention.

We claim:

1. A cross connector traversing a spinal column and connecting a pair of spinal fixation rods extending along the spinal column, the cross connector comprising:
    a first part, the first part comprising a first hook at a first end thereof to couple to a first of the pair of spinal fixation rods, a connection bore at a second end opposite the first end thereof to couple to the second part, the connection bore having a first diameter and a second diameter greater than the first diameter such that the connection bore forms a recessed area with a counterbore formed at the second diameter, and a first arm traversing a first portion of the spinal column between the first end and the second end;
    a second part, the second part comprising a second hook at a first end thereof to couple to a second of the pair of spinal fixation rods, a shank end at a second end opposite the first end thereof to couple to the first part, and a second arm traversing a second portion of the spinal column between the first end and the second end; and
    a coupling device to couple the first part to the second part, the coupling device having a coupling device shank to extend through the connection bore and a socket through which the shank end extends such that the first arm is pivotally and rotationally connected to the second arm, a coupling device nut, the coupling device shank having a threaded end configured to extend through the connection bore
    a first pad, the first pad to engage the first of the pair of spinal fixation rods opposite the first hook, the first pad and the first hook having surfaces to cooperatively engage the first of the pair of spinal fixation rods, and the first pad having a necked-down portion;
    a second pad, the second pad to engage the second of the pair of spinal fixation rods opposite the second hook, the second pad and the second hook having surfaces to cooperatively engage the second of the pair of spinal fixation rods, and the second pad having a necked-down portion;
    the first pad and the second pad being movable between an attached position where the surfaces cooperatively engage the spinal fixation rods and an un-attached position where the cross connector can be fitted onto the spinal fixation rods;
    a first groove in the first part, the first pad being movable in the first groove between the attached position and the un-attached position, the first groove having a ledge, and the necked-down portion of the first pad and the ledge of the first groove configured to selectively position the first pad with respect to the first part;
    a first setscrew bore in the first part to receive a first setscrew, the first setscrew moving being threadable to move the first pad between the attached position and the un-attached position;
    a second groove in the second part, the second pad being movable in the second groove between the attached position and the un-attached position, the first groove having a ledge, and the necked-down portion of the second pad and the ledge of the second groove configured to selectively position the second pad with respect to the second part; and
    a second setscrew bore in the second part to receive a second setscrew, the second setscrew being threadable to move the second pad between the attached position and the un-attached position.

2. The cross connector of claim 1, wherein the surfaces of the first pad and the first hook and the surfaces of the second pad and second hook engage the pair of spinal fixation rods such that the first part and the second part can rotate about the longitudinal axis of the rods.

3. The cross connector of claim 1, wherein the shank end further comprises a protrusion at a free end, wherein the protrusion inhibits the shank end from being removed from the socket.

4. The cross connector of claim 1, wherein the second part comprises a plane traversing surface such that the first arm traverses the first portion of the spinal column in a first plane and the second arm traverses the second portion of the spinal column in a second plane different than the first plane.

5. The cross connector of claim 1, wherein the first part comprises a plane traversing surface such that the first arm traverses the first portion of the spinal column in a first plane and the second arm traverses the second portion of the spinal column in a second plane different than the first plane.

6. The cross connector of claim 1, wherein the connection bore first diameter defines a shoulder, the shoulder extending around an entire circumference of the connection bore.

7. The cross connector of claim 1, wherein the first pad has a curved rod engaging surface and a curved opposing surface defining a pad thickness.

8. The cross connector of claim 7, wherein the curved opposing surface is adapted to engage a first setscrew.

9. The cross connector of claim 1, wherein the coupling device shank has an inner surface adapted to mate with a countertorque device.

10. The cross connector of claim 1, wherein the connector nut is configured to remain entirely outside of the connection bore and couple to the connector shank outside of the connection bore to releasably couple the first arm to the coupling device and the shank extends into the socket to movably couple the second arm to the connector, a surface on the shank end contacts an edge on the connection bore, the coupling device configured to move in the counterbore of the recess as the coupling device nut is threaded on the coupling device shank until the surface contacts the edge, and wherein a height between the first part and second part can be adjusted by moving the coupling device shank in the connection bore and a distance traversed between the first part and second can be adjusted by moving the shank end in the socket.

11. A cross connector for coupling between a first spinal rod and a second spinal rod, the cross connector comprising:
  a first elongate member having a curved end adapted to engage the first spinal rod, a first middle portion, and a first end defining a bore, the bore having a first diameter and a second diameter greater than the first diameter such that the bore forms a recessed area with a counterbore formed at the second diameter;
  a second elongate member having a curved end adapted to engage the second spinal rod, a second middle portion, and a second end defining a shank;
  a connector connecting the first elongate member and the second elongate member, wherein the connector comprises a connector shank, a connector nut and a connector bore, the connector shank being configured to extend through the bore in the first elongate member, and the connector bore adapted to receive the shank of the second elongate member, the connector nut being configured to couple to the connector shank to releasably couple the first elongate member to the connector, the connector nut configured to remain entirely outside of the bore when tightened sufficient to prevent movement of the first and second elongate members relative to the connector;
  a first pad, the first pad to engage the first spinal rod opposite the curved end of the first elongate member, the first pad and the curved end of the first elongate member having surfaces to cooperatively engage the first spinal rod, and the first pad having a necked-down portion;
  a second pad, the second pad to engage the second spinal rod opposite the curved end of the second elongate member, the second pad and the curved end of the second elongate member having surfaces to cooperatively engage the second spinal rod, and the second pad having a necked-down portion;
  the first pad and the second pad being movable between an attached position where the surfaces cooperatively engage the spinal fixation rods and an un-attached position where the cross connector can be fitted onto the spinal fixation rods;
  a first groove in the first elongate member, the first pad being movable in the first groove between the attached position and the un-attached position, the first groove having a ledge, and the necked-down portion of the first pad and the ledge of the first groove configured to selectively position the first pad with respect to the first elongate member;
  a first setscrew bore in the first elongate member to receive a first setscrew, the first setscrew moving being threadable to move the first pad between the attached position and the un-attached position;
  a second groove in the second elongate member, the second pad being movable in the second groove between the attached position and the un-attached position, the first groove having a ledge, and the necked-down portion of the second pad and the ledge of the second groove configured to selectively position the second pad with respect to the second elongate member; and
  a second setscrew bore in the second elongate member to receive a second setscrew, the second setscrew being threadable to move the second pad between the attached position and the un-attached position.

\* \* \* \* \*